US006214792B1

(12) United States Patent
Simon

(10) Patent No.: US 6,214,792 B1
(45) Date of Patent: Apr. 10, 2001

(54) METHOD FOR TREATING ACUTE AND SEVERE DIARRHEA

(76) Inventor: David Lew Simon, 40 B Eastbrook Heights, Mansfield Center, CT (US) 06250

( * ) Notice: Subject to any disclaimer, the term of this patent is extended or adjusted under 35 U.S.C. 154(b) by 0 days.

(21) Appl. No.: 09/435,564

(22) Filed: Nov. 8, 1999

Related U.S. Application Data

(63) Continuation-in-part of application No. 09/082,260, filed on May 20, 1998, now abandoned, which is a continuation-in-part of application No. 08/631,081, filed on Apr. 12, 1996, now Pat. No. 5,783,583.

(51) Int. Cl.[7] ........................ A61K 38/00; A61K 31/40; A01N 43/36
(52) U.S. Cl. ................................ 514/9; 514/424
(58) Field of Search .......................... 514/9, 424

(56) References Cited

U.S. PATENT DOCUMENTS 5,789,411 * 8/1998 Gooberman et al. ................ 514/255

* cited by examiner

*Primary Examiner*—Dwayne C. Jones
(74) *Attorney, Agent, or Firm*—Cummings & Lockwood

(57) ABSTRACT

The invention provides a method for treating acute and severe diarrhea such as that which accompanies chemotherapy and rapid narcotic detoxification. The method includes administering octreotide in an amount sufficient to alleviate the diarrhea without precipitating clinically significant bradycardia. In a preferred embodiment an anticholinergic is administered together with octreotide to further reduce the possibility of significant bradycardia. The invention also provides a method for rapidly detoxifying a patient addicted to narcotics. Acute and severe diarrhea is eliminated during detoxification by administering octreotide in according to the above-described method.

26 Claims, No Drawings

METHOD FOR TREATING ACUTE AND SEVERE DIARRHEA

RELATED APPLICATIONS

The present application is a continuation-in-part of, commonly owned application Ser. No. 09/082,260, filed on May 20, 1998, abandoned on Nov. 17, 1999, which is a continuation-in-part of, commonly owned application, Ser. No. 08/631,081, filed Apr. 12, 1996, now U.S. Pat. No. 5,783,583, and entitled 17- (cyclopropylmethyl)-4,5-alpha-epoxy-6-methylenemorpinan-3, 14-idiol-hydrochloride salt For the Purpose of Rapid Narcotic Detoxification (hereinafter "the '081 application").

FIELD OF THE INVENTION

The present invention relates generally to a method for treating acute and severe diarrhea as may occur during chemotherapy or acute narcotic withdrawal. More particularly, the present invention provides such a method utilizing the somatostatin analogue octreotide.

BACKGROUND OF THE INVENTION

Acute and severe diarrhea may occur in many circumstances. However clinically significant diarrhea is commonly seen during cancer chemotherapy and during the acute phase of withdrawal in persons addicted to narcotics such as heroin and methadone.

Newer techniques for treating narcotic addiction entail purposefully precipitating an acute withdrawal reaction by the administration of narcotic antagonist drugs such as naloxone, naltrexone or nalmefene. For example, the '081 application, herein incorporated by reference, discloses rapid detoxification methods using the opioid antagonist nalmefene. As disclosed in the '081 application, the addicted patient is given a 1.0 mg intravenous bolus of nalmefene, followed by a intravenous infusion of 1.0 mg nalmefene some time after the initial bolus. Approximately 10 hours after the nalmefene is infused, another 1.0 mg dose of parenteral nalmefene may be given, such as by subcutaneous or intramuscular injection. Approximately 10 hours later a final intramuscular or subcutaneous bolus dose of nalmefene can be given, thereby completing a cycle of parenteral administration of nalmefene totaling approximately 4.0 mg over a span of time approximately 24 hours.

Alternatively, a loading dose of from about 0.5–1.5 mg to no more than about 1.5–2.0 mg is given, followed by slow intravenous infusion at a rate equivalent to 2.0–3.5 mg/day. This dosage regimen is convenient if the patient is to receive intravenous hydration for treatment of nausea and/or diarrhea as may sometimes be associated with withdrawal from opioids.

A method for treating the acute and severe diarrhea typically precipitated by rapid detoxification procedures is to administer the somatostatin analogue octreotide or lanreotide. While octreotide has proven effective in treating clinically significant diarrhea during rapid detoxification, it is associated with an unacceptable incidence of bradycardia, which in some instances has been so severe as to be life threatening.

It is, accordingly, an object of the invention to provide an effective method for treating acute and severe diarrhea It is a further object of the invention to provide such a method which reduces the incidence of life threatening bradycardia.

It is a still further object of the invention to provide a method of rapid narcotic detoxification which safely and effectively treats the acute and severe diarrhea typically accompanying acute withdrawal.

SUMMARY OF THE INVENTION

The present invention meets the above-stated objects by providing a method for treating acute and severe diarrhea comprising the step of administering octreotide in an amount sufficient to alleviate the diarrhea without precipitating clinically significant bradycardia. Preferably octreotide is administered in a dosage of from about $3 \times 10^{-4}$ to about $14 \times 10^{-4}$ mg/kg of body weight, more preferably, in a dose of about 0.0007 mg/kg of body weight, about 0.025 mg to about 0.1 mg for a 70 kg person. Lanreotide may be administered in a therapeutically equipotent dose.

A preferred embodiment of the invention, the method comprises administering octreotide and/or lanreotide together with an anti-cholinergic such as atropine or glycopyrrolate. When administered with octreotide or lanreotide in the preferred dosage range, glycopyrrolate is administered in a dosage range of about $2 \times 10^{-4}$ to about $6.0 \times 10^{-3}$ mg/kg of body weight and more preferably, in a dosage range of about $7 \times 10^{-4}$ mg/kg to about $2 \times 10^{-3}$ mg/kg of body weight. Atropine is preferably administered in a dosage range of about $2 \times 10^{-4}$ mg/kg to about $6.0 \times 10^{-3}$ mg/kg of body weight, more preferably about $2.0 \times 10^{-3}$ to about $5.0 \times 10^{-3}$ mg/kg of body weight and yet, more preferably, about $1.4 \times 10^{-3}$ to $4.5 \times 10^{-3}$ mg/kg of body weight. In a preferred embodiment, octreotide is administered in a dosage range of 50 to 75 mcg somatostatin, glycopyrrolate 0.75 to 0.125 mg and/or atropine 0.175 to 0.225 mg, based on a 70 kg body weight. Other anti-cholinergic drugs producing similar antimuscarinic activity with respect to acetylcholine at postganglionic parasympathetic neuroeffector sites in cardiac muscle may be substituted for atropine and/or glycopyrrolate. Lanreotide at therapeutically equipotent doses to the octreotide doses specified may be employed in lieu of the octreotide. Lanreotide may also be admixed with octreotide to form a mixture which may be employed in lieu of the octreotide or lanreotide alone. Preferably the mixture has therapeutic activity equipotent to that produced by doses of octreotide referenced herein.

In a particularly preferred embodiment of the invention, about 60 to about 75 micrograms of octreotide is combined with approximately 0.1 mg glycopyrrolate and 0.2 mg atropine. A compatible preservative may be used, such as benzyl alcohol, and pH may be adjusted to physiological levels by addition of, for example, hydrochloric acid, sodium hydroxide or sulfuric acid. Clinical experience has demonstrated an embodiment comprising 60 mg octreotide with 0.2 atropine and 0.1 mg glycopyrrolate is particularly effective when typically administered every 6 to 12 hours, most commonly every 8 to 12 hours, for a 70 kg adult human.

The proportions of atropine, octreotide and glycopyrrolate as embodied in one embodiment of the present invention may be prepared by mixing 0.5 cc of a 0.2 mg/cc concentrate of glycopyrrolate with 0.5 cc of a 0.4 mg/cc concentrate of atropine and 0.3 cc of a 200 mg/cc concentrate of sandostatin. Alternatively, 0.5 to 0.75 cc of a 100 mg/cc concentrate of octreotide can be mixed with these same amounts of atropine and glycopyrrolate.

The present invention also provides a method and apparatus for reducing the negative effects of psychological/physiological withdrawal. The method and apparatus ameliorates withdrawal symptomology by reducing the psychological "cue response" evidenced in addicts upon display of a needle-like protuberance. A cue response is elicited when a triggering event—such as seeing or being administered a syringe with a needle-like protuberance—initiates a craving for the drug previously associated cognitively or subconsciously with said syringe having the needle-like protuberance. Commonly, a human addicted to an opioid agonist drug, such a heroin, associates the effects of the drug with the sight and usage of a syringe with a needle-like protuberance. Even when heroin is not used or administered, the cue response may elicit a craving for heroin upon the mere appearance or usage of a syringe with a needle-like protuberance. According to the invention, administration of the octreotide and/or anti-cholinergic drug, and other drugs given to the addict to alleviate or ameliorate withdrawal symptoms, is performed using an injection device having a concealed needle, or which lacks a needle component. In a preferred embodiment, a needleless jet injection device is used to administer the drugs. Representative needleless injection devices finding use in the present invention are described, for example, in U.S. Pat. Nos. 5,919,159, 5,879,327, 5,704,911, 5,559,302 and 5,569,189, the disclosures of which are incorporated by reference herein.

The present invention also provides a method for rapidly detoxifying a patient addicted to exogenously administered narcotics while effectively treating the acute and severe diarrhea that typically accompanies acute withdrawal. According to the invention, acute clinical withdrawal is induced by administering at least about 0.5–1.5 mg up to about 1.5–2.0 mg of nalmefene, based on the weight of a 70 kg human. The diarrhea associated with such withdrawal is treated by administering octreotide in an amount sufficient to alleviate the diarrhea without precipitating clinically significant bradycardia. In a preferred embodiment octreotide is administered together with an anti-cholinergic, such as atropine and/or glycopyrrolate. Surprisingly it has been found that co-administration of octreotide with anti-cholingeric agents, in particular a atropine/glycopyrrolate mix as set forth in the embodiments above, significantly reduces the abdominal distension associated with octreotide and lanreotide.

DETAILED DESCRIPTION OF THE INVENTION

The present invention will be described in detail in the context of a method for rapidly detoxifying a patient addicted to exogenously administered narcotics. However, it should be understood that the broader aspects of the invention are in no way limited in this regard. In particular, the method of treating acute and severe diarrhea disclosed herein is not limited to the diarrhea associated with acute withdrawal but, instead, is useful in treating clinically significant diarrhea generally, such as the diarrhea associated with chemotherapy.

A method of rapid detoxification as taught by the invention is conducted as follows. A patient addicted to narcotics undergoes intravenous cannulation by either the peripheral or central venous route, and the appropriate intravenous solution is infused intravenously at the required rate for the size and conditions of the patient. Monitors of life function are attached to the patient which may include a pulse oximeter, electrocardiogram patches, a blood pressure cuff attached to a sphygmomanometer and a means to measure the carbon dioxide of the patient's exhaled breath by way of capnography.

A medication to induce unconsciousness is administered, preferably by the intravenous route, in doses appropriate for the patient's weight and medical condition. This medication should be a non-opioid derivative not related to the narcotic classification of drugs, such as midazolam, propofol, sodium pentothal, a combination thereof, or other drugs commonly used to induce unconsciousness. As a specific example, a dose of 0.3 milligrams of midazolam per kilogram of body weight administered intravenously is usually sufficient to produce unconsciousness.

This is typically followed by intravenous administration of a medication such as a depolarizing or non-depolarizing neuromuscular blocking agent to facilitate intubation of the patient's trachea. The endotracheal tube is then secured in the correct anatomic position using usual anesthetic care measures. After stabilization of the patient's life functions as usually done in routine anesthetic management, the patient is administered parenterally about 0.025 mg to about 0.1 mg octreotide, preferably about 0.0007 mg/kg of body weight. This dosage of octreotide is sufficient to prevent the acute and severe diarrhea which frequently accompanies acute detoxification and does not precipitate significant bradycardia. Administering octreotide in this dosage range also does not result in the abdominal distention that is frequently observed at higher dosage levels of octreotide.

Clinical evidence establishes that the incidence of bradycardia which accompanies octreotide administration can be further reduced by combining the above-specified octreotide dosage with an anti-cholenergic such as atropine or glycopyrrolate. As noted previously, glycopyrrolate is preferred and is administered parenterally with the octreotide in an amount ranging from about 0.2 mg to above 0.4 mg glycopyrrolate. However, from about 0.2 mg to about 0.4 mg atropine administered parenterally is also effective.

Administration of the octreotide and/or the anti-cholinergic agent, or other therapeutic agents used in the detoxification procedure, may be by way of a needleless injection device. It has surprisingly been discovered that perceived discomfort and overt symptomology of the overall withdrawal process may be significantly diminished by employment of such devices to administer drugs generally administered via a needle. While not wanting to be limited to any particular hypothesis, it is believed that such diminishment may be due to a decrease in the "cue response," a Pavlovian desire for the patient's drug of abuse upon confrontation with an item mentally associated with the "high". It has been discovered that the visualization of "needles" (like the "bells" in Pavlov's experiments) not only exacerbate the desire for a drug of abuse but also complicate the withdrawal process, heightening the addict's perceived discomfort in the withdrawal process.

After octreotide and glycopyrrolate have been administered and the patient's vital signs are stable, nalmefene is administered parenterally, preferably by intravenous route. For a 70 kilogram adult patient, the typical initial dose of parenteral nalmefene is from about 0.5–1.5 mg to no more than about 1.5–2.0 of nalmefene. The dosage is adjusted proportionally based on the weight of the patient, and the rate of administration of nalmefene may be titrated upward or downward depending on the response of the patient's sympathetic nervous system as evidence by monitoring of life functions and other clinical criteria. Some time thereafter, usually no more than four hours after said administration of nalmefene is complete, the patient can be expected to be detoxified and can be safely rendered back to a state of consciousness. Upon awakening the acute phase of withdrawal with have been completed.

In a second embodiment of this aspect of the invention, the patient is administered a glucocorticoid either prior to or after anesthetization. Acute withdrawal produces an "Addisonian-like" state due to the patient's deceased ability to secrete stress harmones in response to the physiological stress imposed by acute withdrawal. The administration of a glucocorticoid prior to inducing withdrawal assists the patient in mounting an appropriate stress response and therefore further alleviates the acute and severe diarrhea and other "Addisonian-like" signs and symptoms which accompanies rapid detoxification.

The preferred glucocorticoid is hydrocortisone, although it should be understood that the invention is not limited in this regard. Other glucocorticoid well known to those skilled in the art as providing similar pharmacological effects may also be utilized. Hydrocortisone is administered in an amount of from about 25 mg to about 100 mg. It has been clinically established that hydrocortisone is particularly effective in reducing the symptoms of acute withdrawal, such as severe diarrhea, when it is combined with diphenhyramine and ranitidine. Accordingly, at about the time of being anesthetized the patient is given an intravenous infusion of hydrocortisone in the above specified dosage, from about 10 mg to about 100 mg diphenhydramine or equivalent dose of other H1 histamine receptor blocker, and from about 10 mg to about 100 mg ranitidine or equivalent dose of other H2 histamine receptor blocker. The preferable doses for a 70 kg human are 50 mg diphenhydramine and 50 mg ranitidine.

During the post-detoxification period, the patient may be given an anti-diarrheal to alleviate loose stool and diarrhea which frequently accompanies the acute reaction of withdrawal from opioid drugs. The anti-diarrheal loperimide is preferred and is administered enterally in a dosage of from about 4 mg to about 16 mg per day. Alternatively, octreotide administered parenterally in a dose of from about 0.025 mg to about 0.05 mg every 12 hours, preferably 0.0007 mg/kg of body weight every 12 hours, will effectively treat symptoms of diarrhea without causing significant bradycardia. Octreotide is a particularly effective treatment when combined with an anti-cholinergic such as glycopyrrolate in a preferred dose of from about 0.2 mg to about 0.4 mg, in the days following detoxification.

As noted previously, octreotide administered in the above-described dosage range is also an effective treatment for the severe diarrhea which is typically present in other clinical situations, such as patients who are undergoing chemotherapy treatment. As noted above, octreotide is a particularly effective treatment for acute and severe diarrhea when combined with an anti-cholinergic such as atropine or, more preferrably, glycopyrrolate. Thus, the dosage of octreotide is combined with from about 0.2 mg to about 0.4 mg of glycopyrrolate in the preferred method of treating severe diarrhea.

Accordingly, a method for treating acute and severe diarrhea has been disclosed. In addition, a method for rapidly detoxifying a patient addicted to narcotics has also been disclosed, wherein the acute and severe diarrhea typically accompanies acute withdrawal is eliminated without precipitating significant bradycardia or abdominal bloating. While preferred embodiments of these treatment methods have been disclosed, various modifications and substitutions may be made without departing from the spirit and scope of the invention. Accordingly, it is to be understood that the present invention has been described by way of example and not by limitation.

I claim:

1. A method for treating acute and severe diarrhea comprising the steps of;

administering octreotide in a dosage from about $3\times10^{-4}$ to about $14\times10^{-4}$ mg/kg of body weight, together with an anticholinergic agent(s) such that diarrhea is controlled without precipitating clinically significant bradycardia.

2. The method of claim 1, wherein the octreotide is administered in a dosage of about 0.0007 mg/kg of body weight.

3. The method of claim 1, wherein the anticholinergic agent(s) comprises glycopyrolate administered in a dosage from about $2.0\times10^{-4}$ to about $6.0\times10^{-3}$ mg/kg body weight.

4. The method of claim 1 wherein the anticholinergic agent(s) comprises glycopyrolate administered in a dosage from about $1\times10^{-3}$ to about $4.5\times10^{-3}$ mg/kg body weight.

5. The method of claim 1, wherein the anticholinergic agent(s) comprises atropine administered in a dosage from about $2.0\times10^{-4}$ to about $6.0\times10^{-3}$ mg/kg body weight.

6. The method of claim 1 wherein the anticholinergic agent(s) comprises atropine administered in a dosage from about $1.4\times10^{-3}$ to about $4.5\times10^{-3}$ mg/kg body weight.

7. The method of claim 1, wherein the anticholinergic agent(s) possesses similar antimuscarinic activity with respect to acetylcholine at postganglionic parasympathetic neuroeffector sites in cardiac tissue as glycopyrolate administered in a dosage from about $1\times10^{-3}$ to about $4.5\times10^{-3}$ mg/kg body weight.

8. The method of claim 1, wherein the anticholinergic agent(s) possesses similar antimuscarinic activity with respect to acetylcholine at postganglionic parasympathetic neuroeffector sites in cardiac tissue as atropine administered in a dosage from about $1.4\times10^{-3}$ to about $4.5\times10^{-3}$ mg/kg body weight.

9. The method of claim 1 wherein the administration of the octreotide and the anticholinergic agent(s) is by way of a needless jet injector.

10. The method of claim 1 wherein the octreotide is administered subcutaneously.

11. The method of claim 1 wherein the octreotide is administered parenterally.

12. The method of claim 1 wherein the anticholinergic agent(s) is administered subcutaneously.

13. The method of claim 1 wherein the anticholinergic agent(s) is administered parenterally.

14. The method of claim 1, wherein diarrhea is controlled without causing abdominal distention.

15. The method of claim 1, wherein lanreotide is administered in lieu of octreotide.

16. The method of claim 1, wherein the anticholinergic agent(s) comprise about 0.05 mg to about 0.15 mg glycopyrrolate and about 0.1 mg to about 0.3 mg atropine.

17. The method of claim 16, wherein the octreotide is administered in a dose of about 60 mg to about 75 micrograms.

18. A method for treating acute and severe diarrhea comprising the steps of:

administering by way of a needless jet injector octreotide in a dosage from about $3\times10^{-4}$ to about $14\times10^{-4}$ mg/kg of body weight together with one or more anticholinergic agent(s) such that diarrhea is controlled without precipitating clinically significant bradycardia.

19. The method of claim 18, wherein the octreotide is administered in a dosage of about 0.0007 mg/kg of body weight.

20. The method of claim 18, wherein the anticholinergic agent(s) comprises glycopyrolate administered in a dosage from about $2.0 \times 10^{-4}$ to about $6.0 \times 10^{31}$ $^3$ mg/kg body weight.

21. The method of claim 18 wherein the anticholinergic agent(s) comprises glycopyrolate administered in a dosage from about $1 \times 10^{-3}$ to about $4.5 \times 10^{-3}$ mg/kg body weight.

22. The method of claim 18, wherein the anticholinergic agent(s) comprises atropine administered in a dosage from about $2.0 \times 10^{-4}$ to about $6.0 \times 10^{-3}$ mg/kg body weight.

23. The method of claim 18 wherein the anticholinergic agent(s) comprises atropine administered in a dosage from about $1.4 \times 10^{-3}$ to about $4.5 \times 10^{-3}$ mg/kg body weight.

24. The method of claim 18, wherein the anticholinergic agent(s) possesses similar antimuscarinic activity with respect to acetylcholine at postganglionic parasympathetic neuroeffector sites in cardiac tissue as glycopyrolate administered in a dosage from about $1 \times 10^{-3}$ to about $4.5 \times 10^{-3}$ mg/kg body weight.

25. The method of claim 18, wherein the anticholinergic agent(s) possesses similar antimuscarinic activity with respect to acetylcholine at postganglionic parasympathetic neuroeffector sites in cardiac tissue as atropine administered in a dosage from about $1.4 \times 10^{-3}$ to about $4.5 \times 10^{-3}$ mg/kg body weight.

26. The method of claim 18, wherein lanreotide is administered in lieu of octreotide.

* * * * *